United States Patent [19]

Mildenberger et al.

[11] 4,305,749
[45] Dec. 15, 1981

[54] 2-DIHALOGENOMETHYLENE-3-HALOGENO-3-CARBALKOXY-5-OXOPYRROLI-DINES, PROCESS FOR THEIR MANUFACTURE AND THEIR USE AS FUNGICIDAL, BACTERICIDAL AND ALGICIDAL COMPOSITIONS

[75] Inventors: Hilmar Mildenberger; Hans-Gerd Gerber, both of Kelkheim; Karl Matterstock, Hofheim am Taunus; Burkhard Sachse; Peter Hartz, both of Kelkheim, all of Fed. Rep. of Germany

[73] Assignee: Hoechst Aktiengesellschaft, Frankfurt am Main, Fed. Rep. of Germany

[21] Appl. No.: 168,154

[22] Filed: Jul. 11, 1980

[30] Foreign Application Priority Data

Jul. 13, 1979 [DE] Fed. Rep. of Germany ....... 2928305

[51] Int. Cl.³ .................... A01N 37/18; A01N 37/22; C07D 207/16
[52] U.S. Cl. ................................. 71/67; 260/326.41; 260/326.43; 260/326.45; 424/274
[58] Field of Search ...................... 260/326.41, 326.43, 260/326.45; 71/67, 95; 424/274

[56] References Cited

U.S. PATENT DOCUMENTS

| | | | |
|---|---|---|---|
| 3,136,620 | 6/1964 | Bucha et al. | ............................. 71/95 |
| 4,013,445 | 3/1977 | Bellus et al. | .................... 260/326.45 |
| 4,070,370 | 1/1978 | Elliott et al. | .................. 260/326.45 |
| 4,129,573 | 12/1978 | Bellus et al. | .................... 260/326.45 |

FOREIGN PATENT DOCUMENTS 2055075 5/1972 Fed. Rep. of Germany ... 260/326.4

*Primary Examiner*—Alton D. Rollins
*Attorney, Agent, or Firm*—Curtis, Morris & Safford

[57] ABSTRACT

2-Dihalogenomethylene-3-halogeno-3-carboalkoxy-5-oxopyrrolidines of the formula I

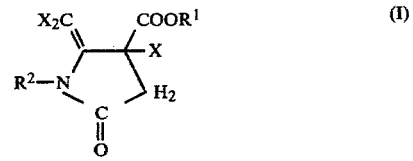

wherein
$R^1$ is hydrogen or $C_{1-4}$ alkyl,
$R^2$ is hydrogen $C_{1-4}$ alkyl, $C_{1-4}$ alkoxycarbonylmethyl, cyclohexyl, benzyl, $C_{1-4}$ alkylphenyl, halogenophenyl, nitrophenyl, $C_{1-4}$ alkoxyphenyl, trihalogenomethylphenyl or $C_{1-4}$ alkoxycarbonylphenyl and
X is halogen, a process for their manufacture and their use as pesticidal compositions.

7 Claims, No Drawings

2-DIHALOGENOMETHYLENE-3-HALOGENO-3-CARBALKOXY-5-OXOPYRROLI-DINES, PROCESS FOR THEIR MANUFACTURE AND THEIR USE AS FUNGICIDAL, BACTERICIDAL AND ALGICIDAL COMPOSITIONS

The present invention relates to novel 2-dihalogenomethylene-3-halogeno-3-carboalkoxy-5-oxo-pyrrolidines of the formula I

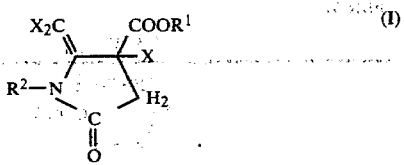

wherein
R$^1$ is hydrogen or C$_{1-4}$alkyl,
R$^2$ is hydrogen C$_{1-4}$alkyl, C$_{1-4}$alkoxycarbonylmethyl, cyclohexyl, benzyl, C$_{1-4}$alkylphenyl, halogenophenyl, nitrophenyl, C$_{1-4}$alkoxyphenyl, trihalogenomethylphenyl or C$_{1-4}$alkoxycarbonylphenyl and
X is halogen.
Preferred radicals in formula I are e.g.,
R$^1$: C$_{1-4}$alkyl,
R$^2$: methyl, methoxycarbonylmethyl, 2,4-dichlorophenyl, 3-trifluoromethylphenyl, benzyl, 2,6-dimethylphenyl, 2-chloro-4-trifluoromethylphenyl, 3-chloro-4-methylphenyl, 3,5-bis-trifluoromethylphenyl, 2,3-dimethylphenyl, 4-ethoxycarbonylphenyl, 4-chlorophenyl, phenyl, 4-methoxyphenyl, 2-methoxyphenyl or 4-bromophenyl and
X: chlorine.
Examples of suitable compounds of the formula I according to the invention wil be listed hereinunder:
2-Dichloromethylene-3-chloro-3-carbomethoxy-5-oxopyrrolidine,
1-Methyl-2-dichloromethylene-3-chloro-3-carbomethoxy-5-oxo-pyrrolidine,
1-Benzyl-2-dichloromethylene-3-chloro-3-carbomethoxy-5-oxo-pyrrolidine,
1-(4-Dichlorobenzyl)-2-dichloromethylene-3-chloro-3-carbomethoxy-5-oxopyrrolidine,
1-(2,4-Dichlorobenzyl)-2-dichloromethylene-3-chloro-3-carbomethoxy-5-oxopyrrolidine,
1-Cyclohexyl-2-dichloromethylene-3-chloro-3-carbomethoxy-5-oxopyrrolidine,
1-Phenyl-2-dichloromethylene-3-chloro-3-carbomethoxy-5-oxopyrrolidine,
1-(4-Methylphenyl)-2-dichloromethylene-3-chloro-3-carbomethoxy-5-oxopyrrolidine,
1-(2,6-Dimethylphenyl)-2-dichloromethylene-3-chloro-3-carbomethoxy-5-oxopyrrolidine,
1-(2-Methyl-6-ethylphenyl)-2-dichloromethylene-3-chloro-3-carbomethoxy-5-oxopyrrolidine,
1-(2,3-Dimethylphenyl)-2-dichloromethylene-3-chloro-3-carbomethoxy-5-oxopyrrolidine,
1-(2,6-Diethylphenyl)-2-dichloromethylene-3-chloro-3-carbomethoxy-5-oxopyrrolidine,
1-(4-Ethoxycarbonylphenyl)-2-dichloromethylene-3-chloro-3-carbomethoxy-5-oxopyrrolidine,
1-(4-Chlorophenyl)-2-dichloromethylene-3-chloro-3-carboethoxy-5-oxopyrrolidine,
1-(2,4-Dichlorophenyl)-2-dichloromethylene-3-chloro-3-carbomethoxy-5-oxopyrrolidine,
1-(2,6-Dichlorophenyl)-2-dichloromethylene-3-chloro-3-carbomethoxy-5-oxopyrrolidine,
1-(3,5-Dichlorophenyl)-2-dichloromethylene-3-chloro-3-carbomethoxy-5-oxopyrrolidine,
1-(4-Bromophenyl)-2-dichloromethylene-3-chloro-3-carbomethoxy-5-oxopyrrolidine,
1-(4-Fluorophenyl)-2-dichloromethylene-3-chloro-3-carbomethoxy-5-oxopyrrolidine,
1-(4-Methoxyphenyl)-2-dichloromethylene-3-chloro-3-carbomethoxy-5-oxopyrrolidine,
1-(2-Methoxyphenyl)-2-dichloromethylene-3-chloro-3-carbomethoxy-5-oxopyrrolidine,
1-(3-Trifluoromethylphenyl)-2-dichloromethylene-3-chloro-3-carbomethoxy-5-oxopyrrolidine,
1-(3,5-bis-Trifluoromethyl)-2-dichloromethylene-3-chloro-3-carbomethoxy-5-oxopyrrolidine,
1-(2-Chloro-4-trifluoromethylphenyl)-2-dichloromethylene-3-chloro-3-cabomethoxy-5-oxopyrrolidine,
1-(3-Chloro-4-methylphenyl)-2-dichloromethylene-3-chloro-3-carbomethoxy-5-oxopyrrolidine,
1-(3-Chloro-6-methylphenyl)-2-dichloromethylene-3-chloro-3-carbomethoxy-5-oxopyrrolidine,
1-(4-Nitrophenyl)-2-dichloromethylene-3-chloro-3-carbomethoxy-5-oxopyrrolidine,
1-(2-Chloro-6-methylphenyl)-2-dichloromethylene-3-chloro-3-carbomethoxy-5-oxopyrrolidine, Subject of the present invention moreover is a process for the manufacture of compounds of the formula I, which comprises reacting 2-methyl-3-carboalkoxypyrrolinones of the formula II

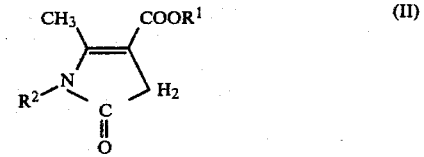

wherein R$^1$ and R$^2$ have the meanings indicated in formula I, with a halogen, preferably in inert solvents.

The preferred halogen is chlorine.

The reaction temperature is not critical and may vary between −10° and +60° C., preferably between 5° and 30° C.

Suitable inert solvents are any compounds that are inert towards the reactants, in particular towards the halogenation agent, under the reaction conditions. Preferred solvents are those that are liquid at the reaction temperature. Examples of preferred solvents are halogenated hydrocarbons, in particular, for example, carbon tetrachloride, methylene chloride, chloroform, or organic acids, in particular, for example acetic acid.

3 Gram equivalents of halogen are used in accordance with the present invention per mol of compound of the formula II.

Some of the compounds of the formula I are difficulty soluble in the reaction mixture and may be isolated by suction-filtration, or they may be obtained in the form of an oil upon evaporation of the solvent used, this oil crystallizing upon trituration with an ether or petrol. The compounds may be further purified by recrystallization from non-polar solvents or by chromatography.

The 2-methyl-3-carboalkoxypyrrolinones of the formula II used as the starting material may be prepared by known methods from acetylsuccinic acid esters and amines (cf., for example W. D. Emery, Liebigs Ann. Chem. 260,137 (1980); A. Cohen, J. chem. Soc., 1950, 3005; M. Pesson et al. Compt. rend. C 272,478 (1971)). Suitable amines for their preparation are in general all primary aliphatic and aromatic amines as well as ammonia.

The compounds according to the invention of the formula I exhibit a relatively broad biocidal effectiveness against fungi, bacteria and algae. They are especially effective against phytophatogenic fungi such as *Botrytis cinerea, uredos, Cercospora betae, Cladosporium fulvum, Fusicladium dendriticum, Piricularia oryzae* and *Rhizoctonia solani*. The compounds according to the present invention have an outstanding effectiveness against Oomycetes belonging to the class of Phytomycetes, for example Phytophthora, Peronospora, Pseudoperonospora, Plasmopora and Pythium.

The compounds are moreover suitable for combating nonphytopathogenic fungi and bacteria that grow on technical substrates, where they may provoke decomposition or destruction. Examples hereof are inter alia *Aureobasidium pullulans, Ulocladium sonsortiale, Aspergillus niger, Penicillium funiculosum, Poria monticola* and *Coniophora puteana*. The compounds according to the invention moreover inhibit the growth of species of bacteria such as *Bacillus subtilis, Aerobacter aerogenes* and *Escherichia coli*.

The compounds of the invention are moreover effective against various species of algae such as *Chlorella vulgaris, Anabaena flos-aquae,* Spirogyra spp. and Enteromorpha spp..

Subject of the present invention therefore also are fungicidal, bactericidal and algicidal compositions characterized by a content of a compound of the formula I.

The fungicidal, bactericidal and algicidal compositions may be formulated in usual manner, for example as dusts, wettable powders, dressings, dispersions, solutions or emulsion concentrates. The content of active ingredient of the formula I in the compositions according to the invention generally is in the range from about 2 to 95 weight %, preferably from 10 to 90 weight %. Said formulations of active ingredients may moreover contain adhesives, wetting agents, dispersing agents, emulsifiers, penetrating agents, solvents, fillers or carriers, which are usual for the intended purpose.

The claimed compounds of the formula I are moreover suitable for use in the technical field, for example in wood preservatives, in paints or for use as preservatives, for example in cooling lubricants for the metal processing.

The present invention will be illustrated by the following examples:

A. PREPARATION EXAMPLES

Example 1

26.6 g (0.1 mol) of 1-(4-chlorophenyl)-2-methyl-3-carbomethoxy-5-pyrrolinone are dissolved in 100 ml of glacial acetic acid. 21.3 g (0.3 mol) of chlorine are added at 10° to 15° C. The chlorination mixture is left to stand overnight at room temperature, whereupon residual chlorine is blown out with nitrogen and the solvent is distilled off in vacuo leaving 36 g of a light brown oil that crystallizes upon trituration with isopropyl ether. The isopropyl ether portion is suction-filtered which gives 28.1 g (corresponding to 76% of the theory) of 1-(4-chlorophenyl)-2-dichloromethylene-3-carbomethoxy-3-chloro-5-oxopyrrolidine of melting point 159° C.

Examples 2 to 30

These examples are carried out in analogous manner to Example 1. The following Table 1 indicates the radicals $R^1$, $R^2$ and X in formula I of the compounds obtained according to these examples by halogenating the corresponding compounds of the formula II, as well as the melting points of the compounds of formula I obtained.

TABLE 1

Formula I:

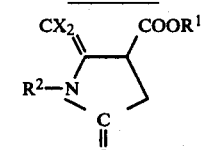

| Example No. | $R^1$ | $R^2$ | X | $M_p$ [°C] |
|---|---|---|---|---|
| 2 | CH₃— | H— | Cl | 154 |
| 3 | CH₃— | CH₃— | Cl | 103 |
| 4 | CH₃— | C₆H₅—CH₂— | Cl | 104 |
| 5 | CH₃— | C₆H₁₁— | Cl | 111 |
| 6 | CH₃— | CH₃—C₆H₄— | Cl | 177 |
| 7 | CH₃— | 2,6-(CH₃)₂C₆H₃— | Cl | 132 |
| 8 | CH₃— | 2,3-(CH₃)₂C₆H₃— | Cl | 164 |
| 9 | CH₃— | H₅C₂OOC—C₆H₄— | Cl | 133 |
| 10 | CH₃— | 2,4-Cl₂C₆H₃— | Cl | 139 |
| 11 | CH₃— | C₆H₅— | Cl | 161 |
| 12 | CH₃— | O₂N—C₆H₄— | Cl | 142 |
| 13 | CH₃— | 2,6-Cl₂C₆H₃— | Cl | 141 |
| 14 | CH₃— | 2,3-Cl₂C₆H₃— | Cl | 144 |
| 15 | CH₃— | CH₃O—C₆H₄— | Cl | 128 |
| 16 | CH₃— | 2-CH₃O-C₆H₄— | Cl | 124 |

TABLE 1-continued

Formula I:

$$\text{CX}_2=\text{C}(\text{R}^2\text{N})-\text{CH}(\text{COOR}^1)-\text{CH}_2-\text{C}(=O)-$$

(pyrrolidinone ring with R²–N, C=O, and =CX₂, COOR¹ substituents)

| Example No. | R¹ | R² | X | $M_p$ [°C.] |
|---|---|---|---|---|
| 17 | CH₃— | Br—C₆H₄— | Cl | 163 |
| 18 | CH₃— | (CF₃)C₆H₄— | Cl | 149 |
| 19 | CH₃— | (CF₃,Cl)C₆H₃— | Cl | 118 |
| 20 | CH₃— | (CH₃,Cl)C₆H₃— | Cl | 145 |
| 21 | CH₃— | (CH₃,Cl)C₆H₃— | Cl | 121 |
| 22 | CH₃— | (CF₃,CF₃)C₆H₃— | Cl | 110 |
| 23 | CH₃— | (CH(CH₃)₂)C₆H₄— | Cl | 145 |
| 24 | C₂H₅— | Cl—C₆H₄— | Cl | 151 |
| 25 | CH₃— | (Cl,CH₃)C₆H₃— | Cl | 137 |
| 26 | CH₃— | (C₂H₅,C₂H₅)C₆H₃— | Cl | 125 |
| 27 | CH₃— | (C₂H₅,CH₃)C₆H₃— | Cl | 131 |
| 28 | CH₃ | (CH₃,CH₃)C₆H₃— | Cl | 139 |
| 29 | CH₃— | CH₃OOC—CH₂— | Cl | 72 |
| 30 | C₂H₅— | CH₃—C₆H₄— | Cl | 169 |

B. FORMULATION EXAMPLES

Example A

A wettable powder which is easily dispersible in water is obtained by mixing
- 25 parts by weight of active substance,
- 64 parts by weight of quartz containing kaolin as inert material,
- 10 parts by weight of sodium lignosulfonate and
- 1 part by weight of sodium oleoyl-methyl-taurine as wetting and dispersing agent and grinding the mixture in a pin mill.

Example B

A dusting powder suitable for use as fungicidal composition is obtained by mixing
- 10 parts by weight of active substance and
- 90 parts by weight of talc as inert material
and comminuting the mixture in a hammer mill.

Example C

An emulsifiable concentrate is obtained from
- 15 parts by weight of active substance
- 75 parts by weight of cycohexanone as solvent and
- 10 parts by weight of oxethylated nonyl phenol (10 EO) as emulsifier.

Example D

A granular composition is obtained by adsorbing from 2 to 15 parts by weight of active substance in a toluenic solution to an inert granular carrier material having the desired granular size such as attapulgite, granular pumice or quartz sand and by evaporating the solvent.

C. BIOLOGICAL EXAMPLES

The letters A to G employed in the following examples stand for the comparative compositions listed hereinunder:

A: Mangano-ethylene-1,2-bis-dithiocarbamate,
B: N-(trichloromethylthio)-phthalimide,
C: Mixed complex of maneb and zineb (mancozeb),
D: Mergal S 40 (combination of thirame and carbendazime)
E: Mergal AT liquid (combination of zirame, thiurame and carbendazime),
F: Mergal CAB 40 (combination of chloroacetaldehyde and sodium bisulfite),
G: Mergal AF (combination of chloroacetamide, alkali metal fluoride and a quaternary ammonium compound).

Example 1

Tomato plants (Solanum lycopersicum) of the variety Rheinlands, Ruhm, in the 3-leaf stage are sprayed to run-off with the compounds listed in Table I, at active substance concentrations of 500, 250, 125 and 60 mg, respectively, per liter of spray liquor. Composition A is used, by way of comparison.

After the spray coating has dried on, the plants are heavily inoculated with a zoosporangia suspension of Phytophthora and placed, dripping-wet, in a climatically controlled chamber at a temperature of 15° C. and a relative atmospheric humidity of from 85 to 95% for 24 hours. Thereafter the plants are brought into a greenhouse.

After an incubation time of 7 days, the plants are examined for infection with Phytophthora. The degree of infection is expressed in % of infected leaf area relative to the untreated, infected control plants (=% infection). The result is summarized in Table I.

TABLE I

| Compound according to Ex. | leaf area infected with Phytophthora, in %, at x mg of active substance/liter of spray liquor | | | |
|---|---|---|---|---|
| | x = 500 | x = 250 | x = 125 | x = 60 |
| 3 | 0 | 0 | 0–3 | 5 |
| 29 | 0 | 0 | 0–3 | 5 |
| 10 | 0 | 0 | 3–5 | 5 |
| 18 | 0 | 0 | 3–5 | 5 |
| Comp. Composition A | 0 | 3 | 5 | 15 |
| Untreated infected plants | | | 100 | |

Example II

Vines which had been grown from cuttings of the Plasmorpara-prone Müller-Thurgau variety and which were in the 4-leaf stage, are sprayed to run-off with aqueous suspensions of the compounds shown in Table II, at the active substance concentrations of 500, 250, 125 and 60 mg, respectively, per liter of spray liquor. The comparative compositions used are the compositions B and C.

After the spray coating has dried on, the plants are inoculated with a zoosporangia suspension of Plasmopara viticola and placed, dripping-wet, in a climatically controlled chamber at a temperature of 20° C. and a relative atmospheric humidity of 100%. After 24 hours, the infected plants are taken from the chamber and brought into a greenhouse which is at a temperature of 23° C. and at about 80–90% atmospheric humidity.

After an incubation time of 7 days, the plants are moistened and placed overnight in the climatically controlled chamber, the disease thereby being caused to erupt. The infection is subsequently assessed. It is expressed in % of infected leaf area compared to the untreated infected control plants (=100% infection), and is shown in Table II).

TABLE II

| Compound according to Example | % of Plasmopara infection at x mg of active substance/liter of spray liquor | | | |
|---|---|---|---|---|
| | x = 500 | x = 250 | x = 125 | x = 60 |
| 4 | 0 | 0 | 0 | 0 |
| 10 | 0 | 0 | 0 | 3–5 |
| 7 | 0 | 0 | 0 | 3–5 |
| 18 | 0 | 0 | 0–3 | 5 |
| 19 | 0 | 0 | 0 | 0 |
| 20 | 0 | 0–3 | 3 | 5 |
| 22 | 0 | 0 | 0–3 | 5 |
| Comp. Composition | | | | |
| B | 0 | 3 | 5 | 10 |
| C | 5 | 10 | 25 | 35 |
| Untreated infected plants | | 100 | | |

Example III 0.02 ml Portions of a bacteria suspension of Bacillus subtilis in droplet form are aded to a nutrient medium (standard I-nutritive agar-agar for bacteria) on Petri dishes. The compound according to the invention which are specified in the examples have been added to the nutritive medium in liquid form previously at the concentrations of active substance listed in Table III. The commercially available composition D, E, F and G free from Mercury are used for comparative purposes. The Petri dishes are kept at room temperature.

4 Days after inoculation of the dishes, the diameter of the bacteria colonies is measured on the agar-agar medium and the growth inhibition, in %, caused by the compounds applied relative to the control medium (=inoculated agar-agar without addition of active substance=0% inhibition) is determined. The result is summarized in Table III.

TABLE III

| Compound according to Example | Growth inhibition in % of Bacillus subtilis at x mg of active substance per liter of agar-agar | | | | |
|---|---|---|---|---|---|
| | x = 1000 | x = 500 | x = 100 | x = 50 | x = 10 |
| 3 | 100 | 100 | 100 | 100 | 80 |
| 4 | 100 | 100 | 100 | 100 | 50 |
| 7 | 100 | 100 | 100 | 100 | 100 |
| 8 | 100 | 100 | 100 | 100 | 80 |
| 9 | 100 | 100 | 100 | 100 | 50 |
| 10 | 100 | 100 | 100 | 100 | 50 |
| 1 | 100 | 100 | 100 | 100 | 100 |
| 11 | 100 | 100 | 100 | 100 | 50 |
| 15 | 100 | 100 | 100 | 100 | 80 |
| 16 | 100 | 100 | 100 | 100 | 80 |
| 17 | 100 | 100 | 100 | 100 | 80 |
| Comp. Composition | | | | | |
| D | 50 | 25 | 0 | 0 | 0 |
| E | 50 | 25 | 0 | 0 | 0 |
| F | 100 | 50 | 0 | 0 | 0 |
| G | 50 | 25 | 0 | 0 | 0 |
| Untreated infected plants | | | 0 | | |

Example IV 0.02 ml Portions of a spore suspension of Ulocladium consortiale in droplet form are added to a nutritive medium (biomalt agar-agar for fungi) on Petri dishes. The compounds according to the invention which are specified in the examples have been added previously to the agar-agar medium in liquid state at the concentrations of active substance listed in Table IV.

The compositions D, E, F and G free from mercury are used for comparative purposes. The Petri dishes are kept at room temperature. The diameter of the fungi colonies on the agar-agar medium is measured 6 days after inoculation of the Petri dishes and thereafter the growth inhibition, in %, caused by the compounds applied, relative to the control composition (=inoculated agar-agar without addition of active substance=0% inhibition) is determined. The result is summarized in Table IV.

TABLE IV

| Compound according to Example | Growth inhibition in % of *Ulocladium consortiale* at x mg of active substance per liter of agar-agar | | | | | |
|---|---|---|---|---|---|---|
| | x = 1000 | x = 500 | x = 100 | x = 50 | x = 10 | x = 5 |
| 3 | 100 | 100 | 100 | 100 | 90 | 80 |
| 10 | 100 | 100 | 100 | 100 | 90 | 50 |
| Comp. Composition | | | | | | |
| D | 100 | 100 | 100 | 80 | 30 | 0 |
| E | 100 | 20 | 0 | 0 | 0 | 0 |
| F | 100 | 100 | 60 | 0 | 0 | 0 |
| G | 100 | 100 | 80 | 0 | 0 | 0 |
| Untreated infected Agar | | | 0 | | | |

Example 5

0.02 ml Portions of a spore suspensions of *Xanthomonas malvacearum* in droplet form are added to a nutritive medium (biomalt agar-agar for fungi) on Petri dishes. The compounds according to the invention have been added previously to the agar-agar medium in liquid state at the concentrations of active substance listed in Table V. The petri dishes are kept at room temperature. The diameter of the bacteria colonies on the agar-agar medium is measured 4 days after inoculation of the Pertri dishes and the growth inhibition, in %, caused by the compounds applied, relative to the control composition (=inoculated agar-agar without addition of active substance=0% inhibition) is determined. The result is summarized in Table V.

TABLE V

| Compound according to Example | Growth inhibition in % of *Xanthomonas malvacearum* at x mg of active substance per liter of agar-agar | | | |
|---|---|---|---|---|
| | x = 250 | x = 125 | x = 60 | x = 30 |
| 3 | 100 | 100 | 80 | 50 |
| 29 | 100 | 100 | 90 | 50 |
| 4 | 100 | 100 | 50 | 30 |
| Untreated infected Agar | | 0 | | |

Example 6

The mono-cellular green alga *Chlorella vulgaris* in its logarithmic growth phase contained in a nutritive solution (according to Böhler) is treated with the compound according to the invention of Example 4 which is listed in Table VI at the concentration of active substance specified in Table VI. The treatment is carried out in Erlenmeyer flasks of 100 ml volume each containing 30 ml of algae suspension. The test recipients are placed on an agitator with permanent movement (75 rpm), permanent light (about 3,000 lux) and at room temperature. The test is evaluated after 10 days. The degree of destruction, in %, caused by the compound according to the invention, relative to the control (=algae suspension without addition of active substance=0% destruction) is determined. The result is summarized in Table VI.

TABLE VI

| Compound according to Example | Algicidal effectiveness againt *Chlorella vulgaris*, degree of destruction in % at x ppm of active substance | | | |
|---|---|---|---|---|
| | x = 500 | x = 250 | x = 125 | x = 60 |
| 4 | 100 | 100 | 100 | 75 |
| Untreated algae suspension | | 0 | | |

What is claimed is:

1. 2-Dihalogenomethylene-3-halogeno-3-carboalkoxy-5-oxopyrrolidines of the formula I 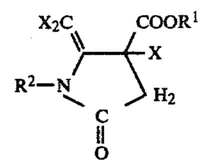 (I)

wherein $R^1$ is hydrogen or $C_{1-4}$alkyl, $R^2$ is hydrogen, $C_{1-4}$alkyl, $C_{1-4}$alkoxycarbonylmethyl, cyclohexyl, benzyl, $C_{1-4}$alkylphenyl, halogenophenyl, nitrophenyl, $C_{1-4}$alkoxyphenyl, trihalogenomethylphenyl or $C_{1-4}$alkoxycarbonylphenyl and X is halogen.

2. A process for the preparation of the compounds of claim 1 which comprises reacting 2-methyl-3-carboalkoxypyrrolinones of the formula II 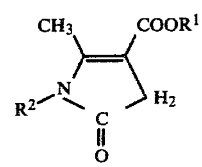 (II)

wherein $R^1$ and $R^2$ are as defined in claim 1, with halogen.

3. The process of claim 2, which comprises conducting the reaction in the presence of an inert solvent.

4. The process of claim 2 wherein said halogen is chlorine.

5. A pesticidal composition containing the compound of claim 1 in an amount not exceeding 95% by weight in admixture with a suitable carrier therefor.

6. A pesticidal composition containing the compound of claim 1 in an amount of from 10 to 90% by weight in admixture with a suitable carrier therefor.

7. Process which comprises applying to a site infected with fungi, bacteria or algae a fungicidally, bacterially or algaecidally effective amount of a composition as defined in claim 1 or 5.

* * * * *